United States Patent [19]

Myers

[11] Patent Number: 5,599,536
[45] Date of Patent: *Feb. 4, 1997

[54] METHOD FOR SUPPRESSING THE ACUTE PHASE RESPONSE IN A PATIENT RECEIVING IL-6 THERAPY

[75] Inventor: Laurie A. Myers, Morris Plains, N.J.

[73] Assignee: Sandoz Ltd., Basel, Switzerland

[*] Notice: The term of this patent shall not extend beyond the expiration date of Pat. No. 5,578,301.

[21] Appl. No.: 166,564

[22] Filed: Dec. 13, 1993

[51] Int. Cl.$^6$ .................................................. A61K 45/05
[52] U.S. Cl. ........................................ 424/85.1; 424/85.2
[58] Field of Search ................................... 424/85.1, 85.2

[56] References Cited

U.S. PATENT DOCUMENTS

| | | | |
|---|---|---|---|
| 5,171,840 | 12/1992 | Kishimoto | 530/350 |
| 5,178,856 | 1/1993 | Burstein | 424/85.2 |
| 5,188,828 | 2/1993 | Goldberg et al. | 424/85.2 |
| 5,299,496 | 7/1993 | Deepey et al. | 530/351 |

FOREIGN PATENT DOCUMENTS

| | | |
|---|---|---|
| 0378171 | 7/1990 | European Pat. Off. . |
| 3027320 | 6/1989 | Japan . |
| 8600639 | 1/1986 | WIPO . |
| 8800206 | 1/1988 | WIPO . |
| 9107988 | 6/1991 | WIPO . |

OTHER PUBLICATIONS

Akira et al., "A Nuclear Factor for IL–6 Expression (NF–IL6) is a Member of a C/EBP Family," *EMBO J.* (1990 Jun.) 9 (6) 1897–1906.

Akira et al., "IL–6 and NF–IL6 in Acute Phase Response and Viral Infection," *Immunol. Rev.,* (1992 Jun.) 127, 25–50.

Akira et al., "Interleukin–6 in Biology and Medicine," Adv. Immunol., (1993) 54, pp. 22–27.

Andus et al., "Recombinant human B cell stimulatory factor 2 (BSF–2/IFN–B2) regulates B–fibrinogen and albumin mRNA levels in Fao–9 Cells," FEBS Lett. 221:18 (1987).

Bataille et al., "Cytokines et Proliferations Lymphoplasmocytaires: Role Essential de L'Interleukine 6", Rev Prat (Paris) 1993, 43, 3, pp. 275–278.

Caracciolo et al., "Human Interleukin–6 Supports Granulocytic Differentiation of Hematopoietic Progenitor Cells and Acts Synergistically with GM–CSF", Blood, vol. 73, No. 3, (Feb. 15), 1989: 666–670.

Castell et al., "Recombinant human interleukin–6 (IL–6/BSF–2/HSF) regulates the synthesis of acute phase proteins in human hepatocytes," FEBS Lett. 232:347 (1988).

Castell et al., "Interleukin–6. The Major Regulator of Acute–Phase Protein Synthesis in Man and Rat," 1989. Ann. N.Y. Acad. Sci., 557: 87–101.

Chang et al., "Phase I Study of Interleukin–6 (IL–6) in Cancer Patients Treated with Ifosfamide, Carboplatin, and Etoposide (Ice)," Blood, 80, 1992 (No. 10, Suppl. 1) Abs. 346.

Demetri et al., "Recombinant Human Interleukin–6 (IL–6) Increases Circulating Platelet Counts and C–Reactive Protein Levels In Vivo: Initial Results of a Phase I Trial in Sarcoma Patients with Normal Hemopoiesis," Blood, 80, 1992, (No. 10, Suppl. 1) Abs. 344.

Fay et al., "Concomitant Administration of Interleukin–6 (rH IL–6) and Leucomax (rh GM–SCF) Following Autologous Bone Marrow Transplantation–A Phase I Trial," Blood 1993, vol. 82, (10, Suppl. 1), p. 431a (abs. 1707).

Gasparetto et al., "Dyshematopoiesis in Combined Immune Deficiency with Congenital Neutropenia," Am. J. Hematol., (1994) 45/1 (63–72).

Gauldie et al., "Interferon $B_2$/B–cell stimulatory factor type 2 shares identity with monocyte–derived hepatocyte–stimulating factor and regulates the major acute phase protein response in liver cells," *PNAS USA* 84: 7251 (1987).

Geiger et al., "Induction of rat acute phase proteins by interleukin 6 in vivo," Eur. J. Immunol. 18: 717 (1988).

Harousseau et al., "Phase I/II trial of recombinant human IL–6 and GM–CSF following autologous bone marrow transplantation for non–Hodgkin's lymphoma," EBMT, Mar. 13, 1994 Harrowgate Meeting.

Heinrich et al., "Interleukin–6 and the acute phase response," Biochem. J. (1990) 265, 621–636.

Iguchi et al., "Effect of Recombinant Human Granulocyte Colony–Stimulating Factor Administration in Normal and Experimentally Infected Newborn Rats," Exp Hematol., (1991 Jun.) 19 (5), pp. 352–358.

Klein et al., "Interleukine 6 et myelome multiple chez l'homme" medicine/sciences 1991; 7: 937–43.

Kushner et al., "Acute Phase Proteins as Disease Markers," in *Disease Markers,* vol. 5, 1–11 (1987).

MacVittie et al., "Therapeutic Efficacy of rh IL–6 in a Nonhvman Primate Model of High Dose, Sublethal, Radiation–Induced Marrow Aplasia," Blood, 80, 1992, (No. 10, Suppl 1), Abs. 347.

McDonald, "The Regulation of Megakaryocyte and Platelet Production," in *Concise Reviews in Clinical and Experimental Hematology,* ed. M. Murphy, AlphaMed Press, Dayton, Ohio (1992) at 161–178.

Metsarinne et al., "Plasma interleukin–6 and renin substrate in reactive arthritis, rheumatoid arthritis, and systemic lupus erythematosus," Rheumatol Int. (1992) 12: 93–96.

Nijsten et al., "serum Levels of Interleukin–6 and Acute Phase Responses," Lancet ii:921 (1987).

Olencki et al., "Phase IA/IB Trial of rhIL–6 in Patients with Refractory Malignancy: Hematologic and Immunologic Effects," Blood, Nov. 15, 1992, vol. 80, No. 10, Suppl. 1 #344.

(List continued on next page.)

*Primary Examiner*—Chhaya D. Sayala
*Attorney, Agent, or Firm*—Robert S. Honor; Melvyn M. Kassenoff; Diane E. Furman

[57] ABSTRACT

A method for ameliorating or suppressing the acute phase response in a patient receiving IL-6 treatment comprises co-administering with the IL-6 an effective amount of granulocyte colony stimulating factor.

17 Claims, 7 Drawing Sheets

OTHER PUBLICATIONS

Patchen et al., "Administration of Interleukin–6 Stimulates Multilineage Hematopoiesis and Accelerates Recovery From Radiation–Induced Hematopoietic Depression," Blood, vol. 77, No. 3, (Feb. 1), 1991, pp. 472–480.

Patchen et al., "Effects of combined administration of interleukin–6 and granulocyte colony–stimulating factor on recovery from radiation–induced hemopoietic aplasia," Experimental Hematology, 21: 338–344 (1993).

Pepys, "Acute Phase Proteins," in *Encyclopedia of Immunology*, Roiitt, I, ed., Academic Press (1992), 16–18.

Rennick et al., "Interleukin–6 Interacts with Interleukin–4 and Other Hematopoietic Growth factors to Selectively enhance the Growth of Megakaryocytic, Erythroid, Myeloid, and Multipotential Progenitor Cells," Blood, vol. 73, No. 7, (May 15), 1989, pp. 1828–1835.

Ryffel et al., "Pathology Induced by Interleukin–6," Toxicology Letters, 64/65, (1992) 311–319.

Sehgal, "Interleukin–6: Molecular Pathophysiology," J Invest Dermatol, 94 (Suppl): No. 6, pp. 2S–6S, (Jun. 1990).

Schipperus et al., "IL–6 enhances the GM–CSF induced in vitro colony formation of myelodysplastic marrow myeloid progenitor cells," Neth. J. Med., 37 (1990), p. A. 34.

Spronk et al., "Plasma concentration of IL–6 in systemic lupus erythematosus; an indicator of disease activity," Clin. exp. Immunol., (1992) 90, 106–110.

Stahl et al., "Effects of Human Interleukin–6 on Megakaryocyte Development and Thrombocytopoiesis in Primates," *Blood*, vol. 78, No. 6 (Sep. 15), 1991: pp. 1467–1475.

Swaak et al., "Interleukin–6 (IL–6) and acute phase proteins in the disease course of patients with systemic lupus erythematosus," Rheumatol Int (1989) 8: 263–268.

Van Snick, "Interleukin–6: An Overview," Annu. Rev. Immunol. 1990, 8: 253–78.

Ballou et al Adv. in Intern. Med. vol. 37, pp. 313–336, (1992).

Mayer et al Exp. Hematol. 19: 688–696 (1991).

Tanikawa et al., Exp. Hematology, vol. 17, pp. 883–888, 1989.

Hamblin, "Cytokine and Cytokine Receptors," IRL Press, Chapter 4, 1993.

Aabrilove et al., J. Natl. Cancer Inst. Monogr., vol. 10, pp. 73–77, 1990.

Fibbe et al., Acta Haematol. (Basel), vol. 86(3), pp. 148–154, 1992.

Neta et al., Lymphokine Res., vol. 7(4), pp. 403–412, 1988.

Scheffner H., Allerg. Immunol., (Leipz.), vol. 36(2), pp. 77–86, 1990.

Akira et al., Adv. Immunol., vol. 54, pp. 1–78, 1993.

METHOD FOR SUPPRESSING THE ACUTE PHASE RESPONSE IN A PATIENT RECEIVING IL-6 THERAPY

BACKGROUND

Hematopoiesis, the proliferation and differentiation of blood cells from pluripotent stem cells, has been found to be regulated by a variety of cell factors (i.e. cytokines), examples of which are the interleukins (IL's) and colony-stimulating factors (CSF's).

Human interleukin-6 (IL-6), in particular, is produced by the lymphoid and other cells and plays a role in stimulating proliferation of multiple lineages of hematopoietic cells. Examples of hematopoietic activities ascribed to IL-6 include antiviral activity, stimulation of B-cells and Ig secretion, induction of IL-2 and IL-2 receptor expression, enhancement of IL-3 induced colony formation, proliferation and differentiation of T-cells, maturation of megakaryocytes, and other functions.

The pleiotropic or multifunctional nature of human IL-6 is reflected in the plurality of names used in the art [e.g., interferon-$\beta_2$ (IFN$\beta_2$), 26 kDa protein (26K), B-cell stimulatory factor 2 (BSF-2), hybridoma/plasmacytoma growth factor (HPGF), hepatocyte stimulating factor (HSF), cytotoxic T-cell differentiation factor (CDF)] to refer to what has been confirmed by molecular cloning to be a single protein of 212 amino acids and a molecular mass ranging from 21 to 28 kd, depending on the cellular source and preparation (see Van Snick, Ann. Rev. Immunol. 1990, 253. Recombinant human IL-6 protein has been molecularly cloned and purified to homogeneity.

The terms "IL-6" and "IL-6 protein" as used herein shall be understood to refer to a natural or recombinantly prepared protein, which may be glycosylated or unglycosylated and which has the amino acid sequence of natural human IL-6 as disclosed, for example, in published PCT application Serial No. WO 88/00206, which is incorporated herein by reference.

A well-documented inter-species activity of human IL-6 comprises stimulation of thrombocytopoiesis, i.e. the process by which megakaryocyte progenitor cells mature into megakaryocytes, from which the platelets are ultimately released into peripheral circulation (see McDonald, "The Regulation of Megakaryocyte and Platelet Production," in *Concise Reviews in Clinical and Experimental Hematology*, ed. by M. Murphy, AlphaMed Press, Dayton, Ohio (1992) at 167).

For example, administration of recombinant human IL-6 (hereinafter also rhIL-6) to normal mice and monkeys has been found to result in increased megakaryocyte size and elevated peripheral blood platelet counts (see, e.g., Stahl et al., *Blood*, Vol. 78, No. 6 Sep. 15, 1991: pp 1467–1475; Mayer et al. Exp. Hematol. 19:688–696).

IL-6 induced platelet production has also been documented in a non-human primate model of radiation-induced marrow aplasia (see, e.g., MacVittie et al., *Blood*, November 15,) 1992, Vol. 80, No. 10), as well as in humans subjected to ICE chemotherapy, Chang et al., *Blood*, id.

The platelets contribute a vital homeostatic function by adhering and coagulating on damaged tissue and by secreting factors which initiate coagulation reactions. A deficiency of platelets (thrombocytopenia) whether caused by failure of platelet production (e.g., as a result of aplastic anemia), and/or megakaryocyte depression brought on by iatrogenic drugs, chemicals or viral infections, AIDS related problems and/or platelet destruction (e.g., as a result of secondary thrombocytopenia), can be a life-threatening condition, for which the only conventional treatments have been repeated platelet transfusions, or bone marrow transplantation, both involving risks of infection and rejection.

Administration of IL-6 to a patient suffering from platelet deficiency may therefore be practiced as an endogenous means of accelerating recovery from thrombocytopenia, and even spare the need for transfusion or transplantation. IL-6 may also be used and particularly important in treating subjects in whom thrombocytopenia has been induced by irradiation or administration of drugs which interfere with hematopoiesis (see Patchen et al., *Blood*, Vol. 77, No. 3 (February 1), 1991: pp. 472–480).

However, administration of IL-6 therapy to a mammalian patient for purposes of obtaining the various benefits and advantages therefrom, including, in particular, stimulation of thrombocytopoiesis, or for other therapeutic purposes, is often accompanied by associated systemic changes which, at higher dosages of IL-6 or over prolonged periods of time, may interfere with attainment of the therapeutic goal.

For example, IL-6 administration has been linked to certain responses by the liver which otherwise typically characterize the mammalian "acute phase response" to a challenge such as inflammation or tissue injury. Symptoms of the acute phase response include alteration in plasma protein levels and steroid concentrations, leukocytosis, increased vascular permeability, fever, patient malaise, discomfort, fatigue, weight loss and pallor (Andus et al., *FEBS Lett.* 221:18 (1987)).

In particular, IL-6 has been found to act on the hepatocytes to regulate production therein of certain plasma proteins typically associated with the acute phase response, which are referred to as "acute phase proteins," see Gauldie et al., *PNAS U.S.A.* 84:7251 (1987); Geiger et al., *Eur. J. Immunol.* 18: 717 (1988)).

Such acute phase proteins include both "up-regulated" proteins, plasma levels of which are increased in response to IL-6 administration, and "down-regulated" proteins, plasma levels of which are depressed by IL-6 (see Pepys, "Acute Phase Proteins," in *Encyclopedia of Immunology*, Roitt, I., ed., Academic Press (1992), 16–18).

Examples of "up-regulated" acute phase proteins include $a_1$-antitrypsin, haptoglobulin, ceruloplasmin, alpha-1-acid glycoprotein, C-reactive protein (CRP), and alpha-2-macroglobulin. An example of a "down-regulated" protein comprises prealbumin (see Mayer et al., *Exp. Hematol.* 19:688–696 (1991)).

The extent of an acute phase response accompanying in vivo administration of IL-6 can be correlated to measurable changes in the serum levels of such circulating acute phase proteins.

Studies in normal rhesus monkeys demonstrate that IL-6 administration may be accompanied by a dose-related increase in serum levels of positively regulated acute phase proteins, such as CRP, alpha-1-glycoprotein, gamma-globulin, $\alpha$-2-macroglobulin and fibrinogen, and likewise, a dose-related decrease in negatively regulated prealbumin, Mayer et al., id.; Ryffel et al., *Toxicology Letters*, 64/64 (1992), 311–319. See also Geiger et al., *Eur. J. Immunol.* 18:717 (1988); Castell et al., *FEBS Lett.* 232:347 (1988); Nijstein et al., *Lancet* ii:921 (1987). In Phase I trials of rhIL-6 in human cancer patients, acute phase proteins including CRP and fibrinogen increased during therapy. Olencki et al., *Blood*, Nov. 15, 1992, Vol. 80, No. 10, Supp. 1, #344, 346.

The occurrence of associated systemic changes comprising an acute phase response in patients can result in patient discomfort, and even become pathologic, to the point where the patient's tolerability of a drug becomes in question. A means of reducing an acute phase response can significantly improve the overall practical utility of therapeutic substances indicated to produce such response.

Granulocyte colony stimulating factor (G-CSF) has been shown to exert a regulatory effect on granulocyte-committed progenitor cells to increase circulating granulocyte levels. In particular, G-CSF can promote an increase in the number of circulating neutrophils, which assist in protecting the body against infection. Accordingly, G-CSF can be particularly useful in accelerating recovery from neutropenia in patients subjected to radiation or chemotherapy, or following bone marrow transplantation, see Dexter, "Granulocyte Colony Stimulating Factor (G-CSF), in *Encyclopedia of Immunology*, id.

The terms "G-CSF" and "G-CSF protein" as used herein shall be understood to refer to a natural or recombinantly prepared protein having the amino acid sequence of natural human G-CSF as disclosed, for example, in U.S. Pat. No. 4,999,291, which is incorporated herein by reference. Recombinant human G-CSF is hereinafter also referred to as "rhG-CSF".

SUMMARY OF THE INVENTION

It has now been found that an acute phase response in a patient receiving IL-6 can be reduced or suppressed by co-administering G-CSF with the IL-6.

In particular, it has been found in accord with the invention that co-administration of at least an equal weight amount of G-CSF with IL-6 can reduce IL-6-mediated changes in circulating levels of acute phase proteins.

These observations support the conclusion that G-CSF, when co-administered in the indicated minimum ratio relative to IL-6, acts in an unknown and unpredictable way to reduce aspects of the acute phase response, without foregoing the primary therapeutic utilities of IL-6, e.g., thrombocytopoiesis, and without lessening the neutrophil stimulation which may be provided by the G-CSF when also administered in an amount to effect such stimulation.

There appears to be no prior recognition in the art that G-CSF may be co-administered with IL-6 to obtain the greater benefits in connection with reducing or suppressing the acute phase response, which are described herein.

The present invention therefore comprises a method for suppressing the acute phase response in a patient receiving IL-6, which comprises co-administering an acute phase protein-reducing effective amount of G-CSF with the IL-6.

The invention also provides therapeutic compositions to be administered in accordance with the method of the invention.

Patients to be treated by the method of the invention include mammals, including human and non-human primates, especially humans.

BRIEF DESCRIPTION OF THE DRAWINGS

FIG. 1 depicts changes in the average platelet count of each group from baseline levels;

FIG. 2 depicts the change in average neutrophil level of each group from baseline levels;

FIG. 3 is a bar graph representing the change in average erythrocyte sedimentation rate (ESR);

FIG. 4 is a bar graph showing the baseline average serum $\alpha$-2-macroglobulin level for each group prior to cytokine administration;

FIG. 5 shows the average serum $\alpha$-2-macroglobulin level following administration of cytokine;

FIG. 6 is a bar graph showing the average baseline serum fibrinogen level for each group prior to cytokine administration;

FIG. 7 is a bar graph showing the average fibrinogen level for each group.

DETAILED DESCRIPTION

Figure 1:
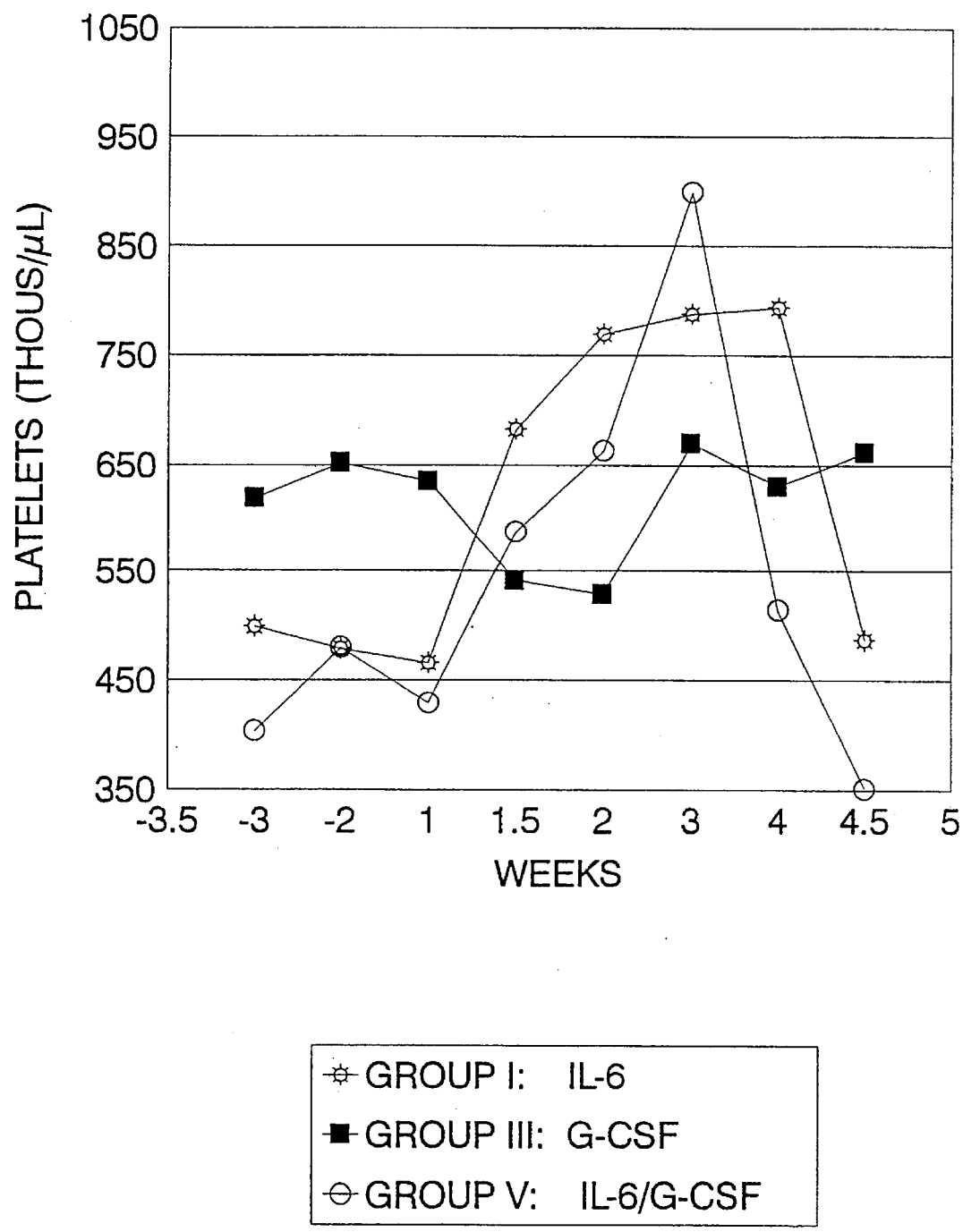
FIGS. 1–7 comprise a series of graphs which demonstrate the effect on various aspects of the acute phase response of administering to rhesus monkeys a course of therapy comprising either of: rhIL-6 (Group I); rhG-CSF (Group III); or rhIL-6 and rhG-CSF (Group V).

The human IL-6 used in the present invention may be purified from natural sources or produced by recombinant means, as is well-known. G-CSF can also be similarly obtained. Preferably, the cytokines are obtained by culturing transformants obtained by transforming a host with recombinant DNA comprising at least the human cDNA under the control of a suitable promoter. Preferred methods of recombinantly producing mammalian IL-6 and G-CSF involve expression in bacteria or yeast cells, although recombinant proteins can also be produced using mammalian cells, insect cells, or other cells under the control of appropriate promoters.

The protein can be glycosylated to varying degrees or unglycosylated.

*E. coli* derived, non-glycosylated rhIL-6 can be obtained by the methods described in published PCT patent application No. WO 88/00206, or can be glycosylated, mammalian cell-produced IL-6, as described therein.

*E. coli*-derived, non-glycosylated rhG-CSF is commercially available from Amgen Inc. (Thousand Oaks, Calif.) under the tradename Neupogen®, and glycosylated forms may be produced by known means.

The natural human IL-6 and G-CSF proteins used in the invention may be modified by changing the amino acid sequence. Thereof, for example, from 1 to 5 amino acids in their sequences may be lengthened, without changing the fundamental character thereof and provide modified proteins which are the full functional equivalents of the native proteins. Such functional equivalents may also be used in practicing the present invention.

The natural or recombinantly prepared proteins, and their functional equivalents used in the method of the invention are preferably purified and substantially cell-free, which may be accomplished by known procedures.

According to the method of the invention, reduction or suppression of the acute phase response in a patient receiving IL-6 therapy can be effectuated by co-administering to the patient an amount of G-CSF which is equal to or greater than the amount of the IL-6, the amount of each being expressed as unglycosylated protein.

As previously indicated, the extent of an acute phase response in a patient receiving IL-6 can be reasonably correlated to changes in serum levels of certain acute phase proteins, in particular CRP, $\alpha$-2-macroglobulin and fibrinogen.

Therefore, the extent of an acute phase response in a subject being administered IL-6 can be determined based on the difference between the baseline serum level of one or more circulating acute phase proteins, i.e. the level prior to initial administration of IL-6, and the serum level of the protein following commencement of IL-6 administration.

The unexpected effect of G-CSF co-administration with the IL-6 can be estimated by comparing the serum level of one or more acute phase proteins taken after initial administration of IL-6 alone, with the serum level taken after G-CSF is co-administered with G-CSF.

Baseline levels of protein may be measured any time prior to IL-6 administration, preferably within 3–4 weeks, and more preferably within 2 weeks or 1 week, prior to the IL-6 therapy.

Post-administration protein levels are preferably determined after four days of administration of the combination and within 24 hours of the IL-6 dosing. Preferably, serum samples are taken before the IL-6 is completely metabolized, most preferably within 6 hours of IL-6 administration to the patient. Periodic monitoring, e.g. every 3–7 days, will take place over the longer treatment periods.

Another means of determining the extent of an acute phase response is by comparing the patient's baseline level of total plasma protein concentration with the level subsequent to IL-6 administration.

Changes in total plasma protein concentration can be monitored by the erythrocyte sedimentation rate (ESR), which is a qualitative measure of the density of the liquid portion of the blood.

Suppression or amelioration of the acute phase response by co-administering G-CSF to subjects receiving IL-6 has been found to be achieved without apparent adverse effect on certain primary therapeutic functions of either cytokine, such as the activity of IL-6 in stimulating thrombocytopoiesis, or of the activity of G-CSF to increase neutrophil production.

According to the method of the invention, a granulocyte colony stimulating factor is co-administered with the IL-6 cytokine.

By "co-administered" is meant administration of the total daily dosage of each respective cytokine within a common time period of no greater than 15 hours, preferably no greater than 8 hours, even more preferably no greater than 4 hours. Preferably, the G-CSF is administered in 2 hours or less of IL-6 administration. More preferably, the G-CSF is administered within 1 hour down to 30 minutes, or even fifteen minutes of IL-6 administration. Optimally, the total daily dosage of both cytokines are administered simultaneously or virtually simultaneously.

If the daily dose of one or both cytokines is divided into smaller doses, then administration of the two cytokines may be made in any time order provided that the complete dose of each cytokine has been administered over a 15-hour period or lesser periods as described above.

A dosage regimen involved in a method for treating the previously mentioned conditions will be determined based on various factors affecting the action of drugs, e.g., body weight, sex and diet of the patient, severity of infection, time of administration, etc.

In general, the IL-6 will be administered in an amount effective to increase the platelet count of the patient. An effective daily dose of IL-6 for such purposes will range from 0.50 to 20 micrograms (µg) per kilogram of body weight expressed as non-glycosylated IL-6, more usually 1 to 8 mg/kg, and preferably 1.0 to 6 µg/kg. The more preferred effective amount of IL-6 usually ranges from 1.5 to 5.0 µg/kg/day. The amount of G-CSF to be administered will be an amount effective to reduce the acute phase response of IL-6 and may be expressed as a weight ratio relative to the IL-6. In particular, the weight ratio of G-CSF to IL-6 will be at least about 1:1 with both the G-CSF and IL-6 being expressed as non-glycosylated protein. Increasing the weight ratio of G-CSF to IL-6 above the 1:1 ratio will further reduce the acute phase response, although ratios above about 8:1, which may be used, will be of less increased benefit or usually unnecessary for optimum effect. Preferably, the weight ratio of G-CSF to IL-6 will be in the range of from 1:1 to 6:1, with very good results indicated at a ratio of 1:1 or somewhat higher, e.g., at least about 2:1 or in the range of from 2:1 to 5:1, both proteins being expressed as a non-glycosylated protein.

It is particularly preferred to also co-administer the G-CSF in an amount sufficient to increase circulating neutrophils. For such purpose, the daily dosage of G-CSF may range from 1 to 20 micrograms (µg) per kilogram of body weight, more usually 1 to µg/kg., preferably from 2 to 8 µg/kg/day and more preferably from 3 to 8 µg/kg/day, expressed as non-glycosylated G-CSF.

An effective treatment with IL-6 to increase platelets will generally take place over several days, typically over a 4 to 21 day period which may be interrupted for a day or two, and which may be repeated after a few days interruption, depending upon the cause of the deficiency in platelets, for example, the periods of chemotherapy treatment.

Typically, the method of the invention will be carried out by administering to a patient a composition comprising the purified protein in conjunction with physiologically acceptable carriers, excipients or diluents such as neutral buffered saline, or saline mixed with serum albumin.

The compositions can be administered parenterally or subcutaneously. Examples of parenteral administration include subcutaneous, intravenous, intra-arterial, intramuscular, and intraperitoneal, with subcutaneous being preferred.

For parenteral administration, the IL-6 and G-CSF will generally be formulated in a unit dosage injectable form (solution, suspension, emulsion), preferably in a pharmaceutically acceptable carrier medium that is inherently non-toxic and non-therapeutic. Examples of such vehicles include without limitation saline, Ringer's solution, dextrose solution, mannitol and normal serum albumin. Neutral buffered saline or saline mixed with serum albumin are exemplary appropriate vehicles. Non-aqueous vehicles such as fixed oils and ethyl oleate may also be used. Additional additives include substances to enhance isotonicity and chemical stability, e.g., buffers, preservatives and surfactants, such as Polysorbate 80. The preparation of parenterally acceptable protein solutions of proper pH, isotonicity, stability, etc., is within the skill of the art.

Preferably, the product is formulated by known procedures as a lyophilizate using appropriate excipient solutions (e.g., sucrose) as a diluent.

The cytokines may be combined before administration to the patient and administered together, or alternatively, can be separately administered. Separate, but substantially concurrent administration is generally preferred.

The therapy may be administered to mammals, particularly primates, including human and non-human primates, and especially humans.

EXAMPLES

Sources of Recombinant Cytokines.

rh IL-6. rhIL-6 was prepared from recombinant *E. coli* as a non-glycosylated, N-methionine terminated protein according to the method described in published PCT patent application WO 88/00206. The rhIL-6 that accumulated intracellularly was extracted from *E. coli* cells expressing IL-6 cDNA from a plasmid vector and purified to homogeneity by a series of known chromatographic steps, including high-performance liquid chromatography (HPLC) and column chromatography. Sodium dodecyl sulfate-polyacrylamide gel electrophoresis (SDS-PAGE) demonstrated the presence of a single Coomassie blue staining band with a purity of greater than 98%. The specific activity was $9.2 \times 10^7$ U/mg protein, assayed using the mouse cell line B13.29 bioassay as basically described by Lansdorp et al., *Current Topics in Microbiology and Immunology*, Vol. 132, Springer-Verlag, 1986, 105–113. The endotoxin content was <0.1 Eu/ml as determined by the Limulus assay (Levin et al., Thomb. Diath. Haemorh 19:186 (1968), limulus amoebocyte lysate; Whittaker MA Bioproducts, Walkersville, Md.)

The IL-6 was formulated into a sodium phosphate buffered saline solution, containing Polysorbate 80, sucrose and glycine, pH about 7.5, and lyophilized. The lyophilizate was reconstituted for the subcutaneous treatment by thawing in water. The solutions had a specific activity of approximately $11.9 \times 10^7$ units/mg protein.

rhG-CSF. (Neupogen®) was obtained from Amgen Inc. (Thousand Oaks, Calif.) Each single vial of Neupogen® contains 300 µg/mL of recombinant *E. coli*-derived non-glycosylated methionyl human G-CSF (R-metHuG-CSF) having a specific activity of $1.0 \pm 0.6 \times 10^8$ U/mg. The protein is formulated in 10 mM sodium acetate buffer at pH 4.0, containing 5% mannitol and 0.004% Tween® 80. The manufacture, purification and formulation of Neupogen® is also described further in the *Physicians Desk Reference*, 1993, at page 605.

In Vivo Administration of Cytokines.

Animals. Fifteen young adult male rhesus monkeys, *Macaca mulatta*, approximately 4 years old, weighing between 3.5 and 6.3 kg., were housed individually in stainless steel squeeze cages in an air-conditioned room. The monkeys were fed Purina Certified Primate Chow and had access to food and water ad libitum. The temperature and humidity were maintained at 78°±2° F. and 50±20%, respectively. Fresh fruit was given daily to supplement the routine food source.

The fifteen monkeys were randomly assigned to five groups containing 3 animals each.

Figure 4:
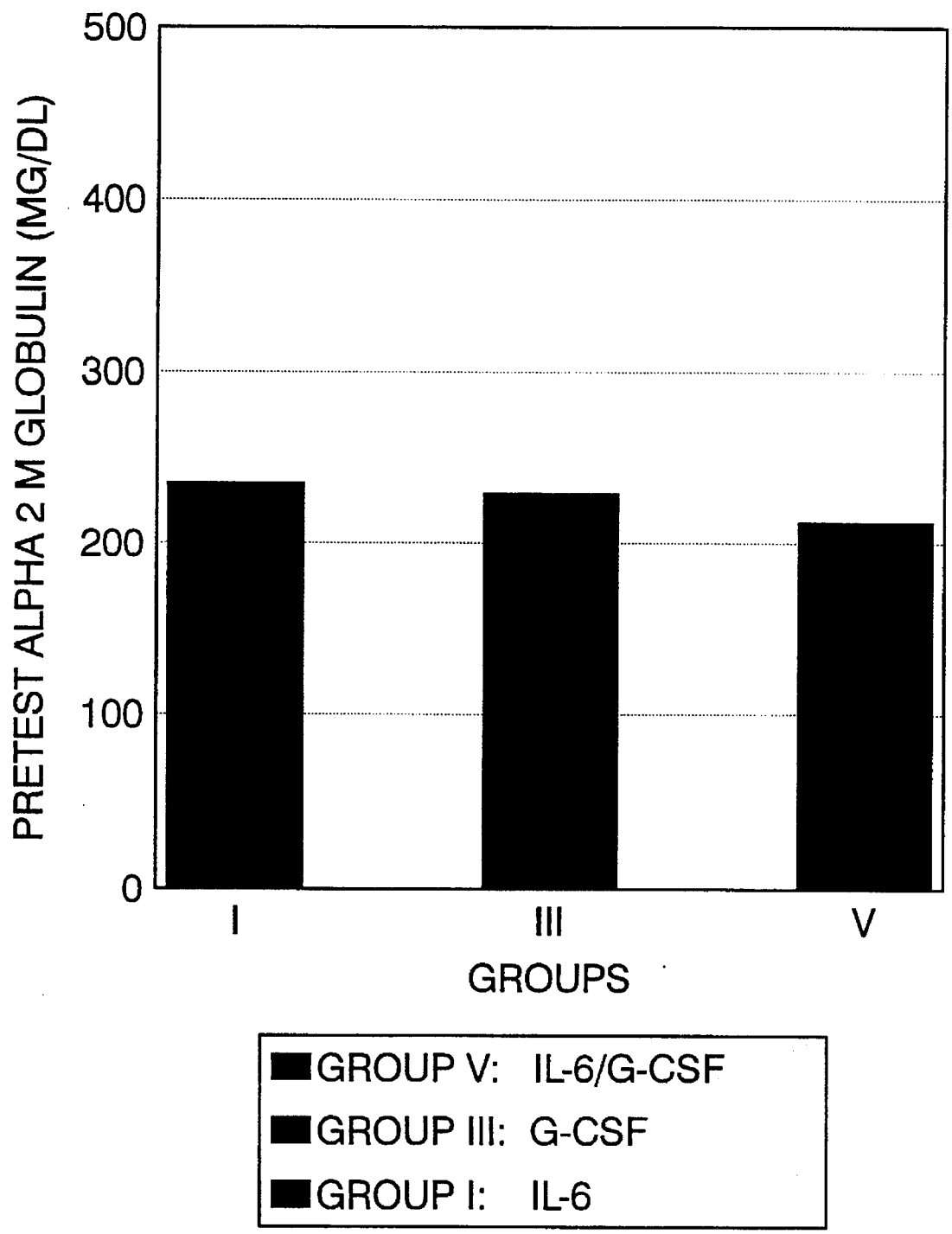
Figure 6:
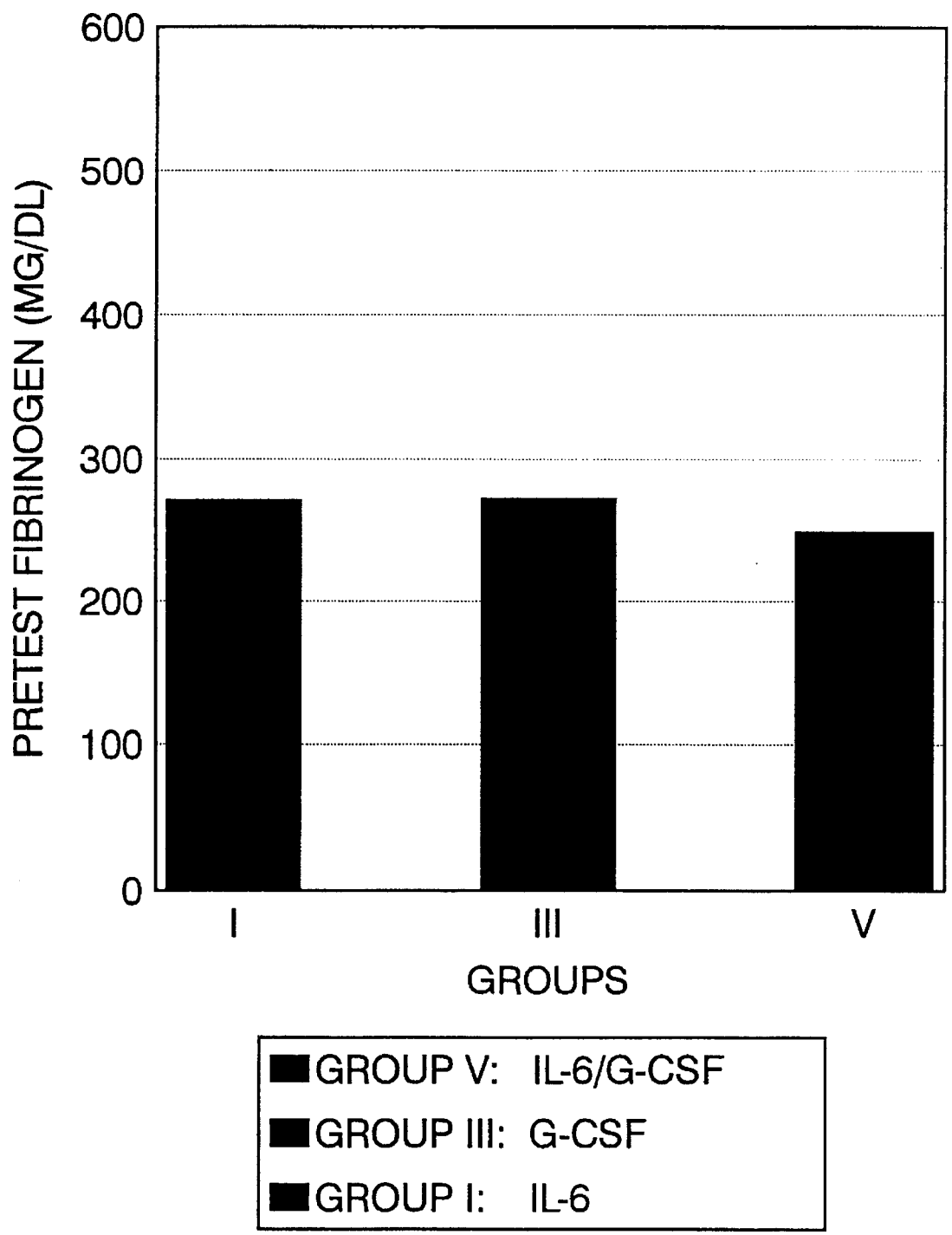

Baseline Levels of alpha-2-macroglobulin and fibrinogen. Alpha-2-macroglobulin and fibrinogen levels (mg/dl) of each test animal were taken to determine base level activity. The average base levels for each group of 3 animals is graphically represented on FIGS. 4 and 6, respectively.

Testing protocol. For a period lasting 30 or 31 days, each animal received a daily subcutaneous injection of IL-6 and/or Neupogen® containing each cytokine in micrograms corresponding to the following dosages:

| Group | Dose of Cytokine (µg/kg/day) |
|---|---|
| Group I | 20 rhIL-6 |
| Group III | 20 rhG-CSF |
| Group V | 20 rhIL-6 + 20 rhG-CSF |

Daily clinical observations and weekly body weights were recorded during weeks −3 to 5. Eye examinations were performed in weeks −3 and 5. Blood was withdrawn for clinical pathology and immunology determinations and testing for baseline levels of platelets, neutrophils, and acute phase proteins, in pretest weeks. Additional blood samples were withdrawn for hematology and immunology evaluations twice in week 1 and once in weeks 2, 3 and 4. On days 30 and 31 necropsy and macroscopic examinations of the tissues were performed. Tissue sections stained with hematoxylin and eosin were examined histologically from each animal. An oil red O section of the liver was examined from all animals on the study. Bone marrow brush smears were prepared at necropsy and evaluated.

Drug-related clinical signs were minimal. All animals survived in good health for the duration of the study.

The following parameters were measured weekly over the duration of the study:

I. Determination of serum proteins of the acute phase response.

(1) Alpha-2-macroglobulin count (mg/dl) was taken using a Boehringer Mannheim/Hitachi 717 analyzer and reagent available from Atlantic Antibodies.

(2) Fibrinogen count (mg/dl) was monitored by an automated Fibrinogen Determination as described by Morse et al., *Amer. J. Clin. Path.* 55 671 (1971).

II. Platelet Count (thousand per milliliter blood) was determined using Coulter Counter Model "S-Plus"; see Coulter Counter Operator's Reference Manual #4201074F/Nov. 1979, Section III, pp. 3–9.

III. Differential Leukocyte Counts were determined using a manual method as described in the following: (1) Approved Laboratory Techinc, Kolmer, Spaulding, Robinson, Fifth Edition, 1959, p. 101; (2) Laboratory Medicine—Hematology, Miale, John B., Second Edition, 1962, p. 811.

IV. Erythrocyte Sedimentation Rate (ESR) was determined by the Wintrobe method of Wintrobe-Landsberg described in Gradwohl's Clinical Laboratory Methods and Diagnosis, Sixth Edition, Volume Two, p. 1151.

No macroscopic findings appeared related to cytokine administration. Microscopic observations that were drug related were limited to spleen, bone marrow and injection sites. A myeloid hyperplasia of the bone marrow which included an increase in neutrophils and eosinophils was detected in the animals which received the combination of IL-6+G-CSF. Injection site reactions included hemorrhage and focal cellular infiltrates. The doses of these factors alone and in combination were well tolerated in these experiments.

DISCUSSION

Figure 2:
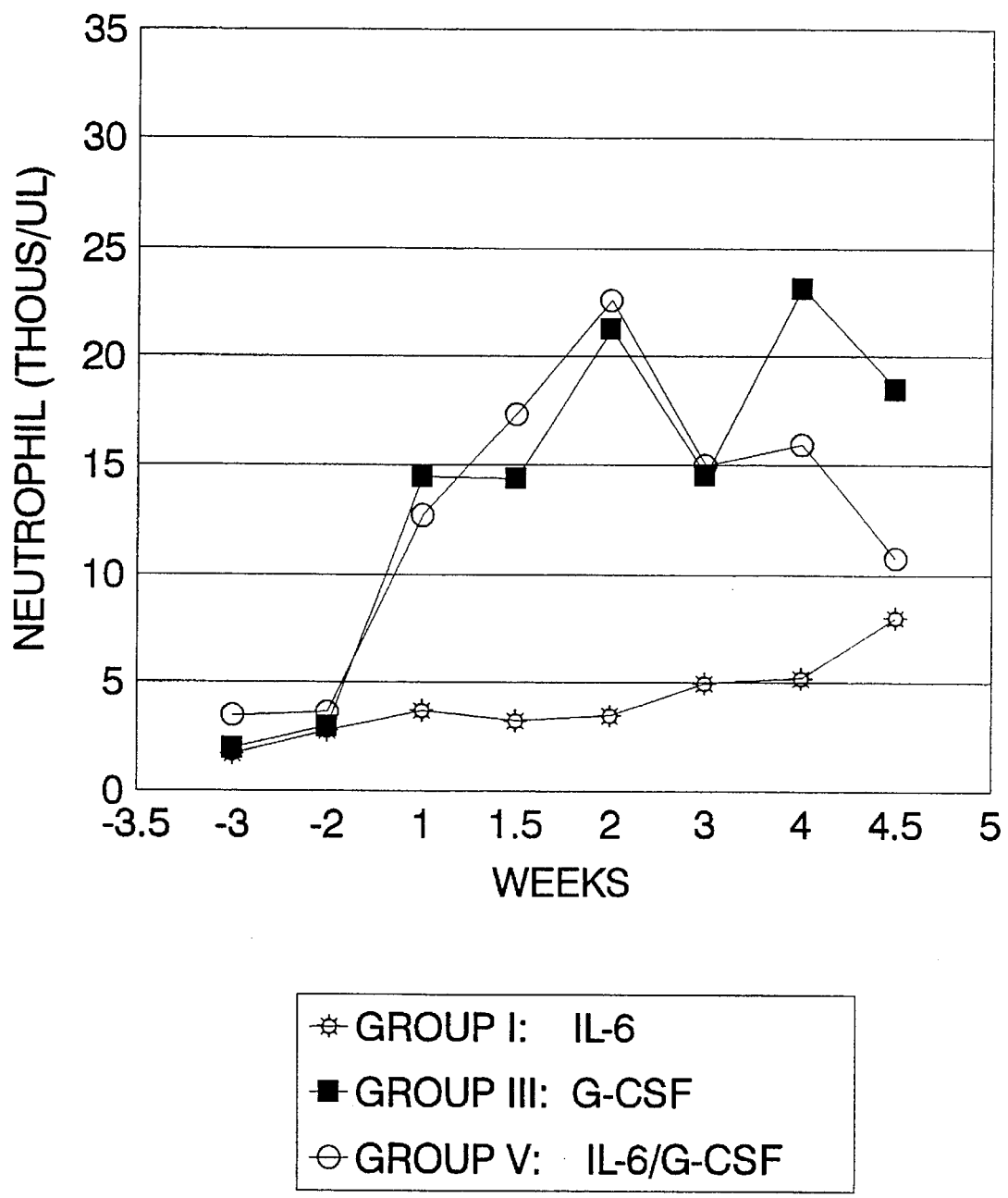
Figure 3:
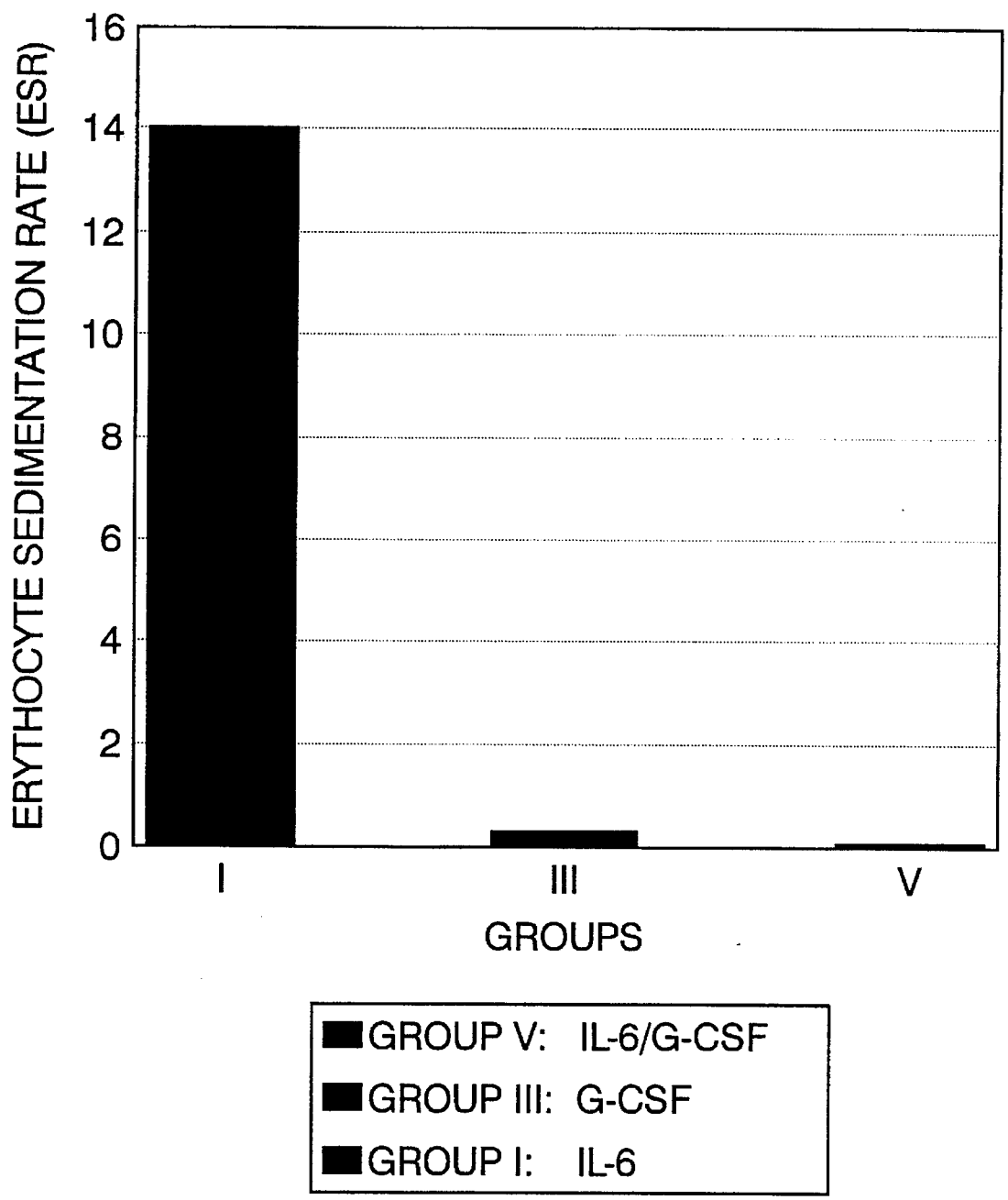
Figure 5:
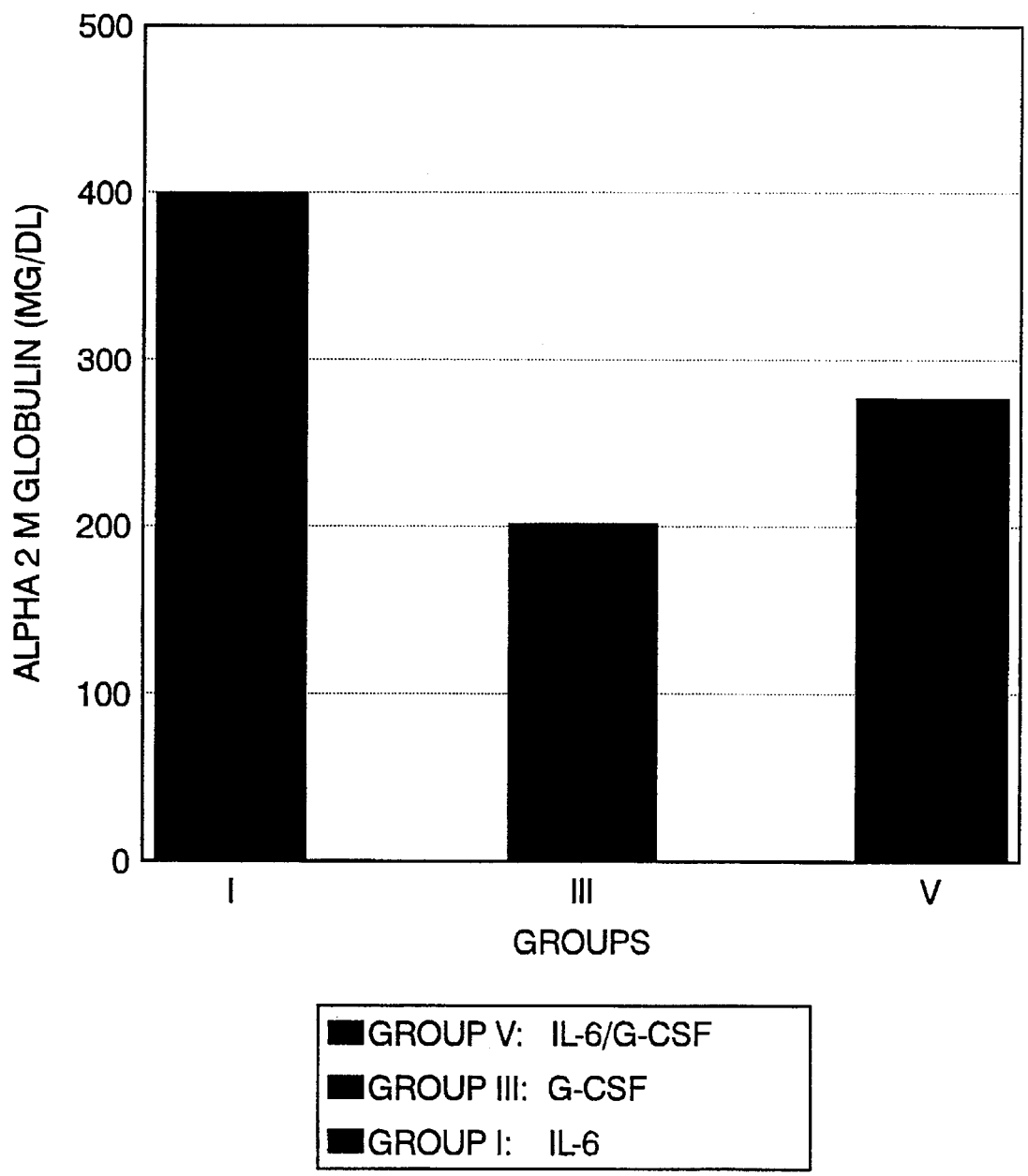
Figure 7:
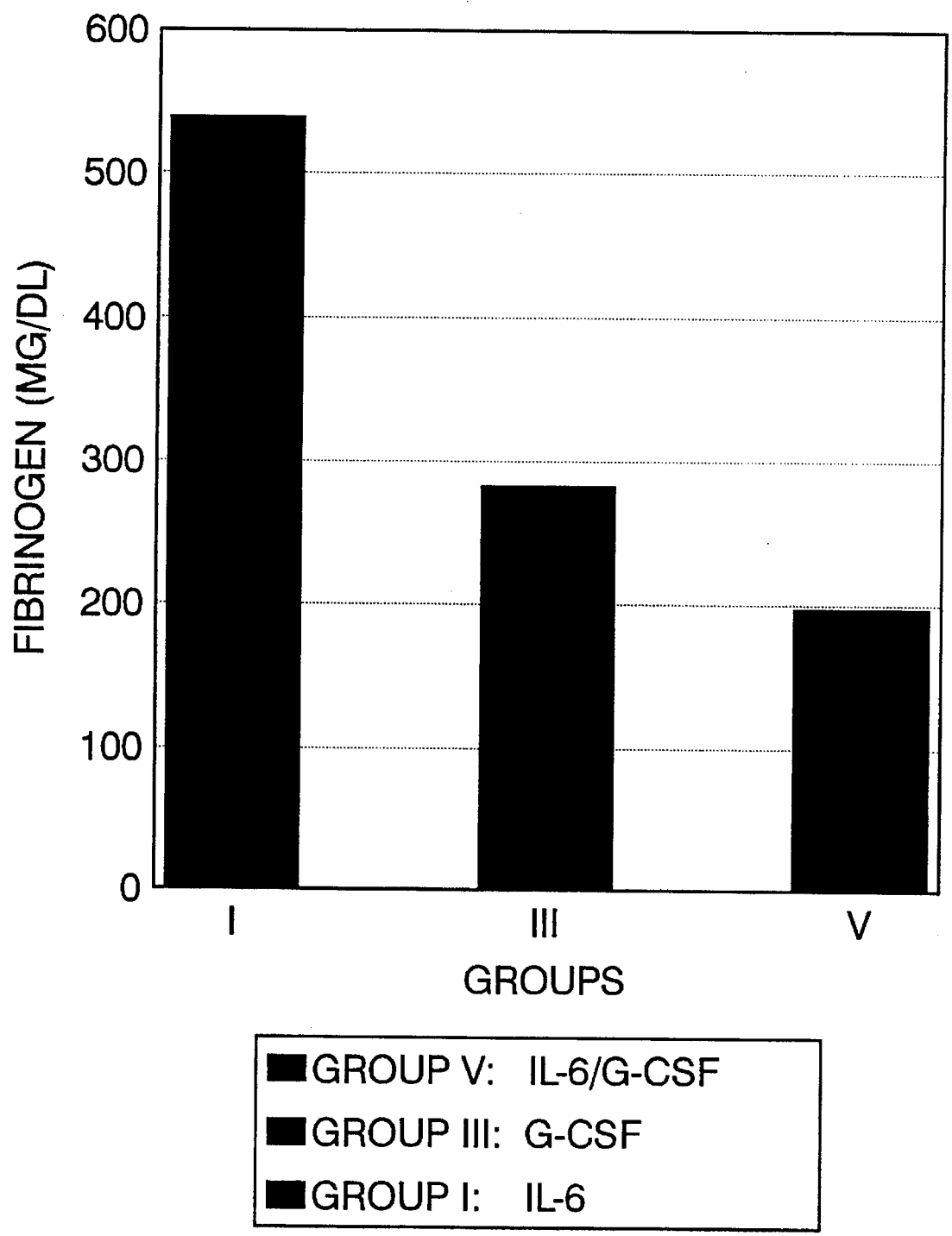

The pharmacological activities noted involved the hematopoietic system and the bone marrow. In general the effects were: IL-6 alone, augmentation of platelets (FIG. 1); G-CSF alone an increase in neutrophils (FIG. 2) and the combination of IL-6+G-CSF, an expansion of the platelets and neutrophils (FIGS. 1 and 2). The acute phase response (characterized by alterations in plasma proteins and alpha-2-macroglobulin levels) was clearly increased in the monkeys which received IL-6 alone (FIGS. 5 and 7), but was significantly reduced when the subjects were administered IL-6 with G-CSF (FIGS. 5 and 7). No other clinical pathology parameters were significantly altered.

What is claimed is:

1. A method for treating the acute phase response in a patient receiving human IL-6 protein, which method comprises co-administering to the patient a platelet count increasing effective amount of human IL-6 protein and an acute phase response-suppressing effective amount of human G-CSF protein, the weight ratio of such G-CSF to such IL-6 being at least 1 to 1 expressed as non-glycosylated proteins, whereby the acute phase response is suppressed.

2. The method of claim 1 in which the human IL-6 protein is administered at a daily dose of from 1.0 to 6.0 micrograms, expressed as non-glycosylated protein per kilogram of patient body weight.

3. The method of claim 2 in which the human G-CSF protein is administered at a daily dose of from 2.0 to 8 micrograms, expressed as non-glycosylated protein, per kilogram of body weight and the weight ratio of human G-CSF protein to human IL-6 protein is at least 2 to 1 expressed as non-glycosylated proteins.

4. The method of claim 1 in which the human G-CSF protein is administered at a daily dose of from 1.0 to 8.0 micrograms, expressed as non-glycosylated protein, per kilogram of patient body weight.

5. The method of claim 1 in which the human IL-6 protein is administered at a daily dose of from 0.5 to 20 micrograms, expressed as non-glycosylated protein, per kilogram of patient body weight.

6. The method of claim 5 in which the human G-CSF protein is administered at a daily dose of from 3 to 8 micrograms, expressed as non-glycosylated protein, per kilogram of patient body weight.

7. The method of claim 6 in which the weight ratio of human G-CSF protein to human IL-6 protein is above 8:1.

8. The method of claim 6 in which the weight ratio of human G-CSF protein to human IL-6 protein is 1:1 to 6:1.

9. The method of claim 6 in which the total daily dosage of both proteins is administered within a common time period of no greater than 15 hours.

10. The method of claim 6 in which the total daily dosage of both proteins is administered within a common time period of no greater than 4 hours.

11. The method of claim 1 in which the human G-CSF protein is administered at a daily dosage of 1 to 20 micrograms, expressed as non-glycosylated protein, per kilogram of body weight.

12. The method of claim 11 in which the weight ratio of human G-CSF protein to human IL-6 protein is from 2:1 to 5:1.

13. The method of claim 12 in which the total daily dosage of both proteins is administered within a common time period of no greater than 8 hours.

14. The method of claim 12 in which the total daily dosage of both proteins is administered within a common time period of 2 hours or less.

15. The method of claim 1 in which the total daily dosage of both proteins is administered within a common time period of no greater than 15 hours.

16. The method of claim 1 in which the total daily dosage of both proteins is administered within a common time period of no greater than 8 hours.

17. The method of claim 1 in which the total daily dosage of both proteins is administered at the same time.

* * * * *